United States Patent [19]

Kronenthal et al.

[11] 3,995,641
[45] Dec. 7, 1976

[54] SURGICAL ADHESIVES

[75] Inventors: Richard L. Kronenthal, Fair Lawn; Edgar Schipper, Highland Park, both of N.J.

[73] Assignee: Ethicon, Inc., Somerville, N.J.

[22] Filed: Apr. 23, 1975

[21] Appl. No.: 571,042

[52] U.S. Cl. .............................................. 128/335
[51] Int. Cl.² ....................................... F24C 15/16
[58] Field of Search .......... 128/335, DIG. 8, 334 R, 128/335.5; 106/161

[56] References Cited
OTHER PUBLICATIONS

Division of Basic Surgical Research Walter Reed Army Institute of Research and US Army Medical Biochemical Research Lab — The Degradation of Cyanoacrylate Tissue Adhesive pp. 424–430 (Surgery Aug. 1965 vol. 58 No. 2).
Plastic and Reconstructive Surgery vol. 30, No. 5, Nov. 1962 pp. 607–610.

*Primary Examiner*—G.E. McNeill
*Attorney, Agent, or Firm*—Wayne R. Eberhardt

[57] ABSTRACT

Carbalkoxyalkyl 2-cyanoacrylates having the formula:

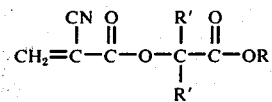

wherein R is an organic radical and R' is hydrogen or methyl polymerize rapidly in the presence of moisture and are useful as adhesives. When applied as tissue adhesives in surgical applications, such carbalkoxyalkyl 2-cyanoacrylates cause a minimum of tissue reaction and the resulting polymer is absorbable in mammalian tissue.

19 Claims, No Drawings

SURGICAL ADHESIVES

FIELD OF THE INVENTION

This invention relates to a new class of cyanoacrylate compositions which are useful as adhesives, and more particularly to compounds which are carbalkoxyalkyl 2-cyanoacrylates. This invention further relates to the use of carbalkoxyalkyl 2-cyanoacrylate monomers as tissue adhesives in surgical applications.

DESCRIPTION OF THE PRIOR ART

Alkyl 2-cyanoacrylates, particularly the methyl, isobutyl and n-butyl 2-cyanoacrylates, have been investigated for use as biological adhesives, as reported for example in Medical World News, 8 (20) 41 (1967); Mfg. Chemist 38 (8), 9 (1967); Technical Report 6618, Walter Reed Army Medical Center, December, 1966. While the unsubstituted alkyl monomers appear to possess the requisite bonding and hemostatic properties when applied to damaged tissues, these materials appear to fail to have the required properties of low toxicity and adequate absorption by the tissues. Methyl 2-cyanoacrylate, for example, gives rise to a severe inflammatory tissue response at the site of application. The n-butyl and isobutyl 2-cyanoacrylate monomers are not absorbed well (if at all) by the tissues and polymeric residue of the adhesive has been observed by histologic examination of the site of application as much as twelve months after surgery as reported in Medical World News, 8 (29), 27 (1967).

It is an object of the present invention to provide cyanoacrylate monomers which are suitable for use in biological adhesive compositions. More particularly, it is an object of the present invention to provide cyanoacrylate monomers which are polymerizable in the presence of blood and other body fluids to form adhesive bonds which do not significantly interfere with natural healing of injured mammalian tissues, and which are readily assimilated by the body with minimal toxic effects.

A further object of this invention is to provide cyanoacrylate monomers which can be used either alone or as comonomers in the bonding of similar or dissimilar materials without the use of heat or catalyst during the bonding operation. Comonomer compositions are of interest for specific uses because they may provide advantageous combinations of properties not completely embodied in individual monomers.

A still further object of this invention is to provide cyanoacrylate monomers which when cast in films, are strong and flexible and particularly well suited for use as wound and burn dressings.

Yet other objects of this invention will be apparent from the description and claims which follow.

SUMMARY OF THE INVENTION

The cyanoacrylates of the present invention are carbalkoxyalkyl 2-cyanoacrylates of the general formula:

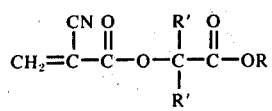

wherein R is an organic radical having from 1 to about 12 carbon atoms and each R' is individually hydrogen or methyl. A particularly preferred class of compounds is carbalkoxymethyl 2-cyanoacrylate.

Monomeric carbalkoxyalkyl 2-cyanoacrylates may be employed individually or as comonomers in biological adhesive compositions and exhibit excellent skin wound adhesion and hemostatic properties. The polymeric products are readily assimilated by the tissues at an acceptable rate and exhibit a relatively low degree of inflammatory tissue response.

DESCRIPTION OF PREFERRED EMBODIMENTS

The carbalkoxyalkyl 2-cyanoacrylates of the present invention are those compounds described by the general formula:

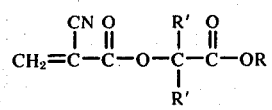

wherein R is an organic radical and each R' is individually hydrogen or methyl.

Organic radical R is not critical to the instant invention and may be any hydrocarbon radical, substituted or unsubstituted, which is convenient to the preparation and use of the carbalkoxyalkyl 2-cyanoacrylate adhesives of the instant invention. Radical R may be straight chain, branched or cyclic, saturated, unsaturated or aromatic.

Typical examples of such organic radicals include $C_{1-8}$ alkyl radicals, $C_{2-8}$ alkenyl radicals, $C_{2-8}$ alkynyl radicals, $C_{3-12}$ cycloaliphatic radicals, aryl radicals such as phenyl and substituted phenyl and aralkyl radicals such as benzyl, methylbenzyl and phenylethyl. Also included are substituted hydrocarbon radicals, particularly halo-, e.g., chloro-, fluoro- and bromo-substituted hydrocarbons, and oxy-, e.g., alkoxy substituted hydrocarbons. Preferred R radicals are alkyl, alkenyl and alkynyl radicals having from 1 to about 8 carbon atoms, and halo substituted derivatives thereof. Particularly preferred are alkyl radicals of 4 to 6 carbon atoms.

Of the carbalkoxyalkyl 2-cyanoacrylates included within the defined scope of the instant invention, carbalkoxymethyl 2-cyanoacrylates wherein each R' is hydrogen and R is an alkyl of from 4 to 6 carbon atoms are particularly preferred for ease of preparation and for efficacy as tissue adhesives. The ensuing specification and examples are accordingly directed primarily toward the preparation and use of such compounds, it being understood that these examples are illustrative only and not limiting of the instant invention.

PREPARATION OF CARBALKOXYMETHYL 2-CYANOACRYLATES

Carbalkoxymethyl 2-cyanoacrylates are prepared by a reaction scheme in which the active vinyl group $$CH_2=C-$$

of an alkyl 2-cyanoacrylate is first blocked by reaction with a conjugated diene such as anthracene to form the Diels - Alder adduct of the ester. The blocking group is maintained during a subsequent two step transesterification of the alkyl cyanoacrylate to a carbalkoxymethyl cyanoacrylate, at which time removal of the blocking group restores the active vinyl group.

The general reaction scheme is illustrated in the following flow chart in which ⒟ represents a cyclic 1,3-diene blocking group.

thionyl chloride, and adduct (III-A) subsequently reacted with an alkyl hydroxyacetate or a methyl substituted alkyl hydroxyacetate to yield the corresponding carbalkoxymethyl 2-cyanoacrylate adduct (IV) or carbalkoxyalkyl 2-cyanoacrylate adduct (IV-A), respectively. The blocking group is finally removed and adduct (IV) or (IV-A) converted into the corresponding

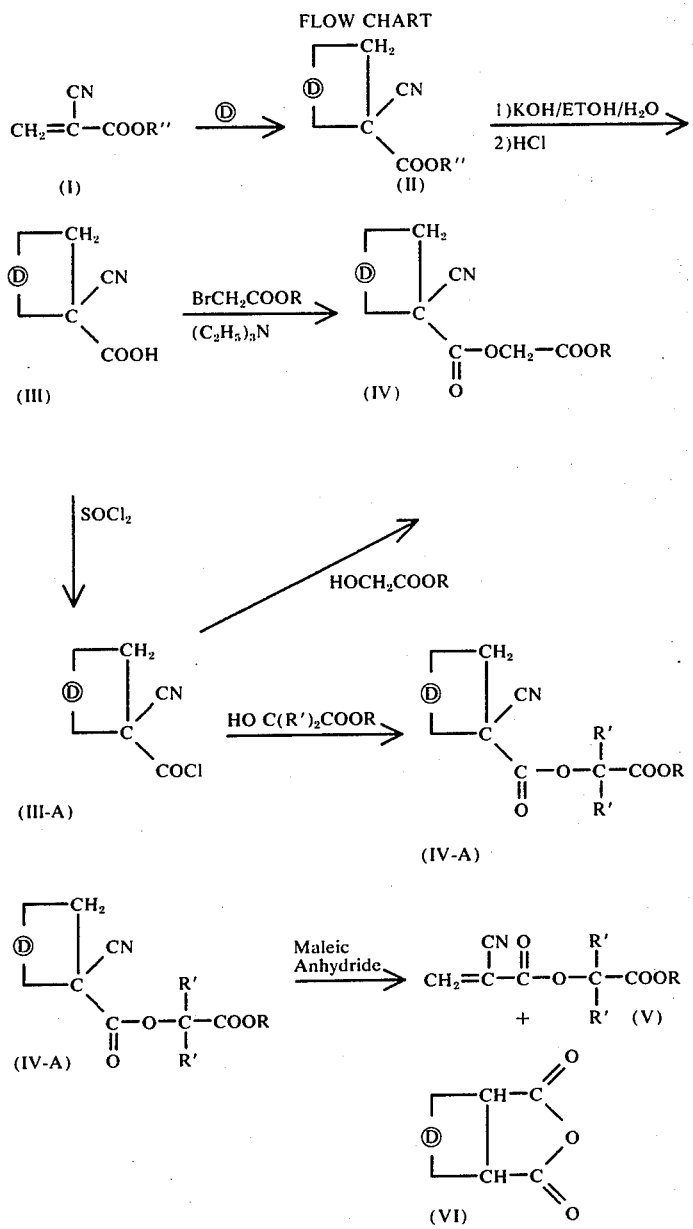

Wherein R'' is any alkyl or alkylene group, preferably alkyl of 1 to 4 carbon atoms and R,R' and ⒟ are as defined above.

With specific reference to the above flow chart, an alkyl ester of 2-cyanoacrylic acid (I) is reacted with a cyclic 1,3-diene to form a Diels - Alder adduct (II). Adduct (II) is subjected to alkaline hydrolysis followed by acidification to form the corresponding 2-cyanoacrylic acid adduct (III). Adduct (III) is preferably esterified by an alkyl bromoacetate to yield the corresponding carbalkoxymethyl 2-cyanoacrylate adduct (IV). Alternatively, adduct (III) may be converted to the 2-cyanoacrylyl halide adduct (III-A) by reaction with carbalkoxyalkyl 2-cyanoacrylate by heating the adduct in the presence of a slight deficit of maleic anhydride.

A particularly preferred 1,3-diene is anthracene, and a typical anthracene adduct of Formula II is represented by the general structure:

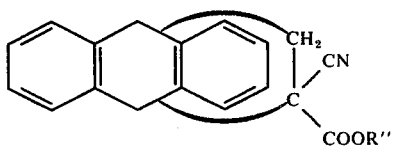

The preparation of alkyl esters of 2cyanoacrylic acid by formation of intermediate Diels - Alder anthracene adducts of the esters, and the subsequent removal of the blocking anthracene group by heating the adduct with maleic anhydride to yield the corresponding alkyl 2-cyanoacrylate monomer is described in U.S. Pat. No. 3,463,804, which patent is incorporated herein by reference.

The alkyl bromoacetates employed in the formation of adduct (IV) are prepared by the reaction of the appropriate alcohols with bromoacetyl bromide in the presence of dimethylaniline. Many of these compounds have been described in J. Agr. Food Chem., 6, 843 (1958). The esterification of an acid with alkyl bromoacetate is discussed in Helv. Chim. Acta, 38, 69 (1955). Both of these publications are incorporated herein by reference.

The preparation of the compounds of the present invention is illustrated by the following examples which are provided for purpose of illustration only and are not limiting of the invention. Unless otherwise noted, all parts and percentages are by weight.

EXAMPLE 1

Preparation of 9,10-Dihydro-9,10-ethanoanthracene-11-cyano-11-carboxylic acid (III)

A mixture consisting of 356.6 g (2.00 moles) anthracene (98+%) and 306.4 g (2.00 moles) isobutyl 2-cyanoacrylate in 2000ml of dry benzene previously treated for 30 seconds with $SO_2$ was refluxed for 188 hours and cooled to room temperature. No unreacted anthracene crystallized from the solution. The solution was solvent stripped on a steam bath at water aspirator pressures to yield a heavy slurry of crystalline solids. Ethanol (500 ml) was added to the slurry and the suspension stripped to a pasty solid residue. This process was repeated with another 2 × 500 ml 95% ethanol in order to strip off the bulk of the residual benzene. The residue was finally diluted with 2000 ml ethanol. A solution of 195 g (3.00 moles) of potassium hydroxide (86%) in 1000 ml $H_2O$ was then added. The reaction mixture was stirred at a moderate reflux for two hours, quenched in 7000 ml water, and the precipitated anthracene (42.5 g, mp 212° – 216° C) filtered off after standing at room temperature overnight. The filtrate was acidified to pH 2.0 with 6N hydrochloric acid, and the precipitated adduct was suction-filtered, washed thoroughly with water, and air-dried to constant weight. The yield of anthracene 2-cyanoacrylic acid adduct (III) was 482.3 g (88% theory), mp 200°–204° C.

EXAMPLE 2

Preparation of Isobutyl bromoacetate

Over a period of 6–8 hours there was added dropwise 1 M of bromoacetyl bromide to a stirred solution of 1 M of isobutyl alcohol, 1 M of dimethylaniline and 200 ml of anhydrous ether. The solution was kept just below boiling by adjusting the rate of addition and by occasional cooling in an ice bath. After complete addition, the mixture was stirred overnight at room temperature. Water (100 ml) was added and the mixture stirred until all of the precipitate had dissolved. The layers were separated and the ether layer was washed with 100 ml portions of 10% sulfuric acid until neutralization of the washings resulted in a clear solution. The washed ether solution was dried over anhydrous sodium sulfate and after removal of the drying agent and solvent the residue was distilled in vacuo. The recovered product had a bp / 14 mm = 72° – 76° C, $n^{25}$ = 1.4468.

The following alkyl bromoacetates were prepared in a like manner from their corresponding alcohols:

Octyl bromoacetate, bp / 0.5 mm = 86°–89° C, $n^{26}$ = 1.4560

Hexyl bromoacetate, bp /0.5 mm = 61°–63° C, $n^{26}$ = 1.4520

Benzyl bromoacetate, bp /0.09 mm = 78°–81° C, $n^{25}$ = 1.5425 n-Butyl bromoacetate, bp /0.8 mm = 37°–39° C, $n^{26.5}$ = 1.4504

2-Butoxyethyl bromoacetate, bp /1.2 mm = 83°–88° C, $n^{25}$ = 1.4849

2-Ethoxyethyl bromoacetate, bp /17 mm = 109°–110° C, $n^{24.5}$ = 1.4575

Allyl bromoacetate, bp /23 mm = 79°–80° C, $n^{26}$ = 1.4715

Cyclohexyl bromoacetate, bp /1.6 mm = 75°–76° C, $n^{24}$ = 1.4847

Propargyl bromoacetate, bp /33 mm = 102°–103° C, $n^{23}$ = 1.4841

Trifluoroethyl bromoacetate, bp /7 mm = 34°–36° C, $n^{25}$ = 1.3935

EXAMPLE 3

General Procedure for the Preparation of Carbalkoxymethyl - 9, 10 - dihydro- 9, 10-ethanoanthracene-11-carboxylates (IV)

To a stirred solution containing molar quantities of 9,10-dihydro-9,10-ethanoanthracene-11-cyano-11-carboxylic acid of Example 1 (hereinafter sometimes referred to as "cyano acid") and triethylamine in 2.25 l of dry ethyl acetate was added dropwise over a period of 30 minutes 1.1 M to 1.5 M of a selected alkyl bromoacetate dissolved in 500 ml of ethyl acetate. The mixture was stirred and refluxed for 6 hours. Water (500 ml) was added in order to dissolve the precipitate. The layers were separated, the aqueous layer was filtered and the filtrate was extracted with 500 ml of ethyl acetate. The extract was added to the original ethyl acetate layer. The combined ethyl acetate layers were washed with consecutive portions of the two times 1500 ml of 1.2 M hydrochloric acid, saturated bicarbonate and water. The washed ethyl acetate solution was dried over anhydrous sodium sulfate. The drying agent was filtered off and the solvent removed in vacuo. The residue, whenever possible, was crystallized by trituration with mixtures of ethyl acetate-hexane (1:10) or ether-pentane (1:10). (The octyl, 2'-ethoxyethyl and 2'-butoxyethyl derivatives did not crystallize and were used as their crude oils in the subsequent deprotection step.) The crystalline products were recrystallized several times from ether or absolute alcohol. The products were identified by elemental analysis and their IR and NMR spectra.

The following specific compounds were prepared according to the above procedure and using indicated reactants.

A. Carbomethoxymethyl 9,10-dihydro-9,10-ethanoanthracene-11-cyano-11-carboxylate Reactants: 137.5 g (0.5 M) cyano acid, 114.8 g (0.75 M) methyl bromoacetate, 50.5 g (0.5 M) triethylamine, 1375 ml ethyl acetate.
Mp 106°–108° C; Yield: 122.5 g (70.6%)
Analysis: Calc'd for $C_{21}H_{17}O_4N$: C: 72.61, H: 4.93, N: 4.03. Found: C: 72.47, H: 5.03, N: 3.94.

B. Carbethoxymethyl 9,10-dihydro-9,10-ethanoanthracene-11-cyano-11-carboxylate Reactants: 137.5 g (0.5 M) cyano acid, 125.3 g (0.75 M) ethyl bromoacetate, 50.5 g (0.5 M) triethylamine, 1400 ml ethyl acetate.
Mp 87°–88° C; Yield: 133.2 g (73.8%)
Analysis: Calc'd for $C_{22}H_{19}O_4N$: C: 73.11, H: 5.30, N: 3.88. Found: C: 73.29, H: 5.35, N: 3.76.

C. Carbo-n-butoxymethyl 9,10-dihydro-9,10-ethanoanthracene-11-cyano-11-carboxylate Reactants: 137.5 g (0.5 M) cyano acid, 121.9 g (0.625 M) n-butyl bromoacetate, 50.5 g (0.5 M) triethylamine, 1.6 l ethyl acetate.
Mp 57°–58° C (recrystallized from ether-petroleum ether); Yield: 92.0 g (47.3%)
Analysis: Calc'd for $C_{24}H_{23}O_4N$: C: 74.02, H: 5.95, N: 3.60. Found: C: 74.29, H: 5.86, N: 3.56.

D. Carbo-i-butoxymethyl 9,10-dihydro-9,10-ethanoanthracene-11-cyano-11-carboxylate Reactants: 137.5 g (0.5 M) cyano acid, 146.3 g (0.75 M) isobutyl bromoacetate, 50.5 g (0.5 M) triethylamine.
The reaction residue from this reaction failed to crystallize after the usual treatment and was taken up in 100 ml of ether. The solution was treated with charcoal and filtered. The filtrate was diluted with 100 ml of pentane. Crystals were obtained by allowing the solution to stand in an icebox and after scratching the inside of the reaction flask. After complete crystallization, the mixture was filtered and the solids were recrystallized several times from absolute ethanol.
Mp 82°–83° C; Yield: 93.7 g (48.2%)
Analysis: Calc'd for $C_{24}H_{23}O_4N$: C: 74.02, H: 5.95, N: 3.60. Found: C: 74.21, H: 5.96, N: 3.57.

E. Carbobenzoxymethyl 9,10-dihydro-9,10-ethanoanthracene-11-cyano-11-carboxylate Reactants: 55 g (0.2 M) cyano acid, 57.3 g (0.25 M) benzyl bromoacetate, 20.2 g (0.2 M) triethylamine, 550 ml ethyl acetate.
Mp 75°–77° C (recrystallized from ether) Yield: 44.5 g (52.7%).
Analysis: Calc'd for $C_{27}H_{21}O_4N$: C: 76.58, H: 5.00, N: 3.31. Found: C: 76.74, H: 5.05, N: 3.30.

F. Carballoxymethyl 9,10-dihydro-9,10-ethanoanthracene-11-cyano-11-carboxylate Reactants: 171.3 g (0.623 M) cyano acid, 139.5 g (0.779 M) allyl bromoacetate, 62.9 g (0.623 M) triethylamine and 1.6 l ethyl acetate.
Mp 112°–113° C (recrystallized from ether) Yield: 167.3 g (71.9%).
Analysis: Calc'd for $C_{23}H_{19}O_4N$: C: 73.98, H: 5.13, N: 3.75. Found: C: 74.09, H: 5.28, N: 3.80.

G. Carbopropargoxymethyl 9,10-dihydro-9,10-ethanoanthracene-11-cyano-11-carboxylate Reactants: 164.5 g (0.6 M) cyano acid, 105.8 g (0.598 M) propargyl bromoacetate, 60.4 g (0.6 M) triethylamine, and 1.6 l ethyl acetate.
Mp 96°–97° C (recrystallized from ether) Yield: 131.5 g (59.6%).
Analysis: Calc'd for $C_{23}H_{17}O_4N$: C: 74.38, H: 4.61, N: 3.77. Found: C: 74.13, H: 4.54, N: 3.75.

H. Carbo-2',2',2'-trifluoroethoxymethyl 9,10-dihydro-9,10-ethanoanthracene-11-cyano-11-carboxylate Reactants: 110 g (0.4 M) cyano acid, 110.5 g (0.5 M) 2,2,2-trifluoroethyl bromoacetate, 40.4 g (0.4 M) triethylamine and 1.3 l ethyl acetate.
Mp 56°–57° C (recrystallized from ether-pentane 3:1) Yield: 117.7 g (70.8%)
Analysis: Calc'd for $C_{22}H_{16}O_4NF_3$: C: 63.61, H: 3.88, N: 3.37. Found: C: 63.92, H: 4.15, N: 3.25.

I. Carbohexoxymethyl 9,10-dihydro-9,10-ethanoanthracene-11-cyano-11-carboxylate Reactants: 206.3 g (0.75 M) cyano acid, 209.1 g (0.938 M) hexyl bromoacetate, 75.8 g (0.75 M) triethylamine, and 2.2 l. ethyl acetate.
Mp 55°–56° C (recrystallized from ether-pentane 1:1) Yield: 201.2 g (64.3%).
Analysis: Calc'd for $C_{26}H_{27}O_4N$: C: 74.80, H: 6.52, N: 3.36. Found: C: 75.05, H: 6.69, N: 3.33.

EXAMPLE 4

General Procedure for the Preparation of Carbalkoxymethyl 2-Cyanoacrylates (V)

A stirred mixture containing 0.25 M of a carbalkoxymethyl 9,10-dihydro-9,10-ethanoanthracene-11-cyano-11-carboxylate of Example 3, 0.24 M of maleic anhydride, 0.5 g hydroquinone and 1.0 g phosphorus pentoxide in 250 ml of anhydrous xylene treated for 30 seconds with sulfur dioxide gas was refluxed for 5 – 18 hours. The anthracene-maleic anhydride was filtered off and the filtrate was solvent stripped under reduced pressure. Acetone (50 ml) was added, any solid matter was filtered off, and the filtrate was again solvent stripped. The residue was treated with 1.0 g of phosphorus pentoxide, subjected to vacuum sublimation at 0.1 mm Hg at a temperature not exceeding 100° C, and finally vacuum distilled at 0.07 mm to 0.2 mm Hg absolute pressure into a receiver containing about 0.05% hydroquinone based on the projected yield of distillate. The final product was stabilized with 300–600 ppm $SO_2$ and the hydroquinone concentration was adjusted to 0.1 percent.

The following specific compounds were prepared according to the above procedure and using the indicated quantities of reactants. All products were identified via elemental analysis and IR and NMR spectra.

A. Carbomethoxymethyl 2-cyanoacrylate

Reactants: 122.5 g (0.353 M) carbomethoxymethyl 9,10-dihydro-9,10-ethanoanthracene-11-cyano-11-carboxylate, 94.1 g (0.339 M) maleic anhydride, 0.7 g hydroquinone, 1.4 g phosphorus pentoxide and 400 ml $SO_2$ treated xylene. Reflux time was 6 hours.
Bp /0.5 mm = 84°–86° C; Yield: 14.0 g (24%).
Analysis: Calc'd for $C_7H_7O_4N$: C: 49.71, H: 4.17, N: 8.28. Found: C: 49.94, H: 4.32, N: 8.27.

B. carbethoxymethyl 2-cyanoacrylate

Reactants: 90.0 g (0.25 M) carbethoxymethyl 9,10-dihydro-9,10-ethanoanthracene-11-cyano-11-carboxylate, 23.5 g (0.24 M) maleic anhydride, 0.5 g hydroquinone, 1.0 g phosphorus pentoxide, 250 ml $SO_2$ treated xylene. Reflux time was 8 hours.
Bp /0.5 mm = 89°–92° C; Yield: 22.7 g (50.5%).
Analysis: Calc'd for $C_8H_9O_4N$: C: 52.46, H: 4.95, N: 7.66. Found: C: 52.42, H: 4.84, N: 7.54.

C. Carbo-i-butoxymethyl 2-Cyanoacrylate (IX)

Reactants: 93.7 g (.241 M) carbo-i-butoxymethyl 9,10-dihydro-9,10-ethanoanthracene-11-cyano-11-carboxylate, 22.7 g (.232 M) maleic anhydride, 0.5 g hydroquinone, 1 g phosphorus pentoxide and 250 ml $SO_2$ treated xylene. The reflux time was 8 hours.
Bp /0.08 mm = 92°–96° C. On standing the distillate crystallized. The crystals had a mp of 28°–29° C. Yield: 32.5 g (66.6%)
Analysis: Calc'd for $C_{10}H_{13}O_4N$: C: 56.86, H: 6.20, N: 6.63. Found: C: 57.17, H: 6.00, N: 6.58.

D. Carbohexoymethyl 2-Cyanoacrylate

Reactants: 200.3 g (0.48 M) carbohexoxymethyl 9,10-dihydro-9,10-ethanoanthracene-11-cyano-11-carboxylate, 45.2 g (0.461 M) maleic anhydride, 1 g hydroquinone, 2 g phosphorus pentoxide and 400 ml $SO_2$ treated xylene. The reflux time was 8 hours.
Bp /0.08 mm = 110°–113° C; Yield 50.9 g (44.9%).
Analysis: Calc'd for $C_{12}H_{17}O_4N$: C: 60.24, H: 7.16, N: 5.85. Found: C: 60.13, H: 7.27, N: 5.71.

E. Carboctoxymethyl 2-Cyanoacrylate

Esterification of 137.5 g (0.5 M) of cyano acid with 157 g (0.625 M) of octyl bromoacetate, 50.5 g (0.5 M) of triethylamine and 1.3 l ethyl acetate was carried out according to the previously described general procedure of Example 3. After workup, there remained 186.9 g (0.42 M, 84.0%) of an oil which did not crystalize, and which was subjected as such to the reaction according to the general procedure of Example 4 above.
Reactants: 39.6 g (.40 M) maleic anhydride, 0.8 g hydroquinone, 1.6 g phosphorus pentoxide, and 400 ml $SO_2$ treated xylene. The reflux time was 8 hours. The product was twice distilled.
Bp /0.07 mm = 119°–121° C; Yield: 30.0 g (27.2%).
Analysis: Calc'd for $C_{14}H_{21}O_4N$: C: 62.90, H: 7.92, N: 5.24. Found: C: 62.82, H: 7.79, N: 5.00.

F. Carballoxymethyl 2-Cyanoacrylate (XII)

Reactants: 140 g (0.375 M) carballoxymethyl 9,10-dihydro-9,10-ethanoanthracene-11-cyano-11-carboxylate, 35.3 g (0.36 M) maleic anhydride, 0.75 g hydroquinone, 1.5 g phosphorus pentoxide, and 400 ml of $SO_2$ treated xylene. The reflux time was 6 hours.
Bp /0.09 mm = 87°–90° C; Yield: 20.8 g (29.6%)
Analysis: Calc'd for $C_9H_9O_4N$: C: 55.38, H: 4.65, N: 7.18. Found: C: 55.70, H: 4.79, N: 7.06.

G. Carbo-n-butoxymethyl 2-cyanoacrylate (XIII)

Reactants: 83.2 g (0.214 M) carbo-n-butoxymethyl 9,10-dihydro-9,10-ethanoanthracene-11-cyano-11-carboxylate, 20.1 g (0.205 M) maleic anhydride, 0.5 g hydroquinone, 0.9 g phosphorus pentoxide, and 230 ml. $SO_2$ treated xylene. Reflux time was 9 hours.
Bp /0.07 mm = 104°–105° C; Yield: 24.3 g (53.8%).
Analysis: Calc'd for $C_{10}H_{13}O_4N$: C: 56.86, H: 6.20, N: 6.63. Found: C: 57.07, H: 5.90, N: 6.45.

H. Carbopropargoxymethyl 2-cyanoacrylate

Reactants: 131.5 g (.354 M) carbopropargoxymethyl 9,10-dihydro-9,10-ethanoanthracene-11-cyano-11-carboxylate, 33.3 g (0.34 M) maleic anhydride, 0.7 g hydroquinone, 1.4 g phosphorus pentoxide, and 350 ml $SO_2$ treated xylene. Reflux time was 7 hours.
Bp /0.07 mm = 94°–95° C; Yield: 7.5 g (11.4%).
Analysis: Calc'd for $C_9H_7O_4N$: C: 55.96, H: 3.65, N: 7.25. Found: C: 56.29, H: 3.71, N: 7.16.

I. Carbo-2',2',2'-trifluoroethoxymethyl 2-cyanoacrylate

Reactants: 100.1 g (0.241 M) carbo-2',2',2'-trifluroethoxymethyl 9,10-dihydro-9,10-ethanoanthracene-11-cyano-11-carboxylate, 22.7 g (0.232 M) maleic anhydride, 0.5 g hydroquinone, 1.0 g of phosphorus pentoxide, and 200 ml $SO_2$ treated xylene. Reflux time was 7 hours. The product spontaneously crystallized during distillation, mp, 66°–67° C.
Bp /0.07 mm = 74°–75° C; Yield: 28 g (51.0%).
Analysis: Calc'd for $C_8H_6O_4NF_3$: C: 40.52, H: 2.55, N: 5.91. Found: C: 40.61, H: 2.51, N: 5.94.

J. Carbo-2'-ethoxyethoxymethyl 2-cyanoacrylate

The crude anthracene adduct was obtained by the esterification of 162.4 g (0.59 M) cyano acid by 154.6 g (0.732 M) of 2'-ethoxyethyl bromoacetate in the presence of 59.7 g (0.59 M) of triethylamine in 2 l ethyl acetate according to the general procedure of Example 3. Yield of crude adduct: 222.5 g (0.549 M) (93%). The crude adduct was reacted according to the general procedure of Example 4 with the following reactants:
Reactants: 51.6 g (0.527 M) maleic anhydride, 1 g hydroquinone, 2 g phosphorus pentoxide, and 550 ml $SO_2$ treated xylene. Reflux time was 8 hours. Yield, after two distillations, 13 g (10.9%).
Analysis: Calc'd for $C_{10}H_{13}O_5N$: C: 52.86, H: 5.77, N: 6.17. Found: C: 52.89, H: 6.00, N: 6.01.

K. Carbo-2'-n-butoxyethoxymethyl 2-cyanoacrylate

The crude anthracene adduct was obtained by the esterification of 192.0 g (0.698 M) cyano acid, 194.5 g (0.872 M) 2'-butoxyethyl bromoacetate in the presence of 70.5 g (0.698 M) of triethylamine and 2.4 l ethyl acetate, according to the general procedure of Example 3. Yield of crude adduct, 269.8 g (0.623 M) (89%). This was reacted according to the general procedure of Example 4 with the following reactants:
Reactants: 58.6 g (0.6 M) maleic anhydride, 1.3 g hydroquinone, 2.6 g phosphorus pentoxide and 600 ml $SO_2$ treated xylene. Reflux time was 6 hours. The reaction residue was distilled at 0.09–0.15 mm and a portion boiling over a range of 117°–136° C was collected. This consisted of a mixture of solid and liquid. The solid was filtered off and the filtrate was subjected in part to two molecular distillations. The material distilled at an outside temperature of 160°–170° C and a pressure of 0.07 mm. IR and NMR established the structure and GC gave a single component purity of 96.6%.

EXAMPLE 5

Preparation of
9,10-Dihydro-9,10-ethanoanthracene-11-cyano-11-carbonyl chloride (III-A)

A mixture consisting of 27.5 g (0.1 M) of cyano acid of Example 1, 14.5 ml (0.2 M) of thionyl chloride, 5 drops of pyridine and 200 ml of dry benzene is stirred and refluxed under nitrogen for two hours. On cooling, the cyano acid chloride adduct (III-A) is filtered off as a crystalline product, washed with dry benzene, and reacted with hydroxyacetate or a methyl substituted hydroxyacetate to yield Compound (IV) or (IV-A) respectively as indicated in the Flow Sheet. The reaction thereafter follows the general procedure for reaction of cyano acid with bromoacetate as set forth in Example 3.

PRODUCT EVALUATION

Several of the cyanoacrylates of Example 4 were evaluated for suitability as absorbable tissue adhesives by determining hydrolytic stability of cyanoacrylate polymers, bond strength using rat skin substrates, and rate of absorption in rat subcutis. The heat of polymerization and the time required to reach maximum exotherm was also determined for each adhesive in a microcalorimetry test since these parameters are significant in certain tissue adhesive applications. Test procedures and results are described below.

HYDROLYTIC STABILITY

Cyanoacrylate polymers were prepared by mixing equal parts by weight of selected cyanoacrylate monomers of Example 4 with reconstituted lyophilized human plasma. The resulting polymer was washed, dried, and pulverized to a powder. From 0.4 to 0.6 grams of powder was stirred into a buffered aqueous solution prepared by dissolving 27 g monobasic sodium phosphate in 1 liter of water and adjusted to a pH of 7.25 by the addition of 50% sodium hydroxide. The temperature of the test solution was maintained at 37° C and polymer weight loss was determined over a period of three months with the following results:

| Cyanoacrylate Monomer | % Weight Loss | | | | |
|---|---|---|---|---|---|
| | 1 wk | 2 wks | 1 mo | 2 mos | 3 mos. |
| a. MeC (Control) | 10.7 | 14.1 | 19.3 | 28.8 | 44.0 |
| b. IBC (Control) | 3.9 | 2.4 | 2.4 | 2.8 | 5.2 |
| c. CEC | 13.5 | 18.6 | 27.5 | 38.3 | 51.3 |
| d. CIBC | 7.7 | 10.2 | 16.8 | 35.2 | 63.4 |
| e. COC | 2.3 | 4.1 | 19.4 | 55.9 | 85.6 |

MeC = methyl 2-cyanoacrylate
IBC = isobutyl 2-cyanoacrylate
CEC = carbethoxymethyl 2-cyanoacrylate
CIBC = carbo-i-butoxymethyl 2-cyanoacrylate
COC = carboctoxymethyl 2-cyanoacrylate As is apparent from the above data, the three cyanoacrylates of the present invention (c, d and e) were hydrolysed or converted to water soluble moieties at a rate somewhat greater than MeC which is generally considered to be quite absorbable, and at a rate considerably higher than IBC, an adhesive of the prior art which is considered to be substantially non-absorbable.

BOND STRENGTH

Bond strength in tissue adhesive applications was determined with regard to the adhesion of freshly harvested rat skin. Strips of rat skin are mounted in holders so that an area of approximately one square centimeter of skin is exposed for adhesion. Two such holders are mounted in opposing jaws of an Instron tensile testing apparatus. One drop of adhesive is applied to the surface of one rat skin, and the skins are brought into contact and held under slight pressure for three minutes. The force required to separate the two skins at a pull rate of 5 inches per minute is then measured and the bond strength calculated in grams/cm$^2$. The following results were obtained.

| Adhesive | Bond Strength g/cm$^2$ |
|---|---|
| a. methyl 2-cyanoacrylate (MeC) | 363 |
| b. isobutyl 2-cyanoacrylate (IBC) | 398 |
| c. carbomethoxymethyl 2-cyanoacrylate (CMeC) | 200 |
| d. carbethoxymethyl 2-cyanoacrylate (CEC) | 376 |
| e. carbo-i-butoxymethyl 2-cyanoacrylate (CIBC) | 330 |
| f. carbo-n-butoxymethyl 2-cyanoacrylate (CBC) | 405 |
| g. carbohexoxymethyl 2-cyanoacrylate (CHC) | 544 |
| h. carboctoxymethyl 2-cyanoacrylate (COC) | 328 |
| i. carballoxymethyl 2-cyanoacrylate (CAC) | 400 |
| j. carbo-2'-ethoxyethoxymethyl 2-cyanoacrylate (CEOEC) | 242 |

As is apparent from the above data, the bond strength of most of the cyanoacrylates of the present invention are comparable to those of MeC and IBC prior art compounds. The CMeC compound tends to be somewhat unstable and tests were performed with partially polymerized material which accounts for the lower bond strength. The CHC compound was unusual in demonstrating exceptionally high bond strength.

MICROCALORIMETRY TESTS

This test measures the heat rise occurring when a 12 microliter drop of cyanoacrylate monomer is added to a 100 microliter sample of plasma substrate contained in the well of a calorimeter. Heat rise is monitored to determine maximum temperature increase and time to reach that maximum. The following results were obtained.

| Adhesive | Heat of Polymerization | |
|---|---|---|
| | ° C | Time, Seconds |
| a. MeC | — | — |
| b. IBC | 3.5 | 9 |
| c. CMeC | 2.0 | 128 |
| d. CEC | 3.0 | 20 |
| e. CIBC | 1.4 | 25 |
| f. CBC | 1.7 | 28 |
| g. CHC | 1.5 | 22 |
| h. COC | 1.1 | 17 |
| i. CAC | 1.7 | 29 |
| j. CEOEC | 2.0 | 25 |

In the above test the MeC sample did not polymerize. Of the remaining data, it is apparent that the adhesives of the instant invention, particularly those of samples (e) through (i), demonstrate significantly lower heats of polymerization than the IBC control with somewhat longer polymerization times.

IN VIVO TESTS

The suitability of the cyanoacrylates of the instant invention for use as absorbable adhesives was finally evaluated in limited in vivo tests in rats. Three to six doses of 0.1 ml each of selected monomers were injected into the dorsal subcutis of a group of forty rats. The rats were sacrificed in groups of five after times ranging from 24 hours to 6 months, and the appearance and weight of the polymerized cyanoacrylate was noted together with a visual observation of tissue reaction. The following data were obtained.

| Tissue Adhesive | Percent Polymer Remaining Weeks After Injection of 0.1 ml of Monomer | | | | | | Appearance At 4 Weeks |
|---|---|---|---|---|---|---|---|
| | 1 | 2 | 4 | 8 | 12 | 16 | 24 |
| CMeC | 50 | 0 | 0 | — | — | — | — | Disintegrated |
| CEC | — | 52 | 10 | — | — | — | — | Disintegrated Solid |
| CIBC | — | 88 | 69 | 29 | 34 | 25 | 25 | Disintegrated Solid |
| CNB | 97 | — | 46 | 29 | 12 | 17 | — | Disintegrated Solid |
| CHC | 92 | — | 61 | 39 | 27 | 17 | 5 | Disintegrated Solid |
| COC | — | 78 | 69 | 50 | 40 | 26 | 12 | Soft, Yellow mass |
| MeC | — | 71 | 52 | 38 | 30 | 15 | 8 | Disintegrated Solid |
| IBC | — | 97 | 77 | 83 | 87 | 82 | 85 | Unchanged |
| CEOEC | — | — | 0 | — | — | — | — | Disintegrated |

It is apparent from the above data that the cyanoacrylates of the instant invention demonstrate good in vivo absorbability, confirming the preliminary results of the hydrolytic stability test.

The following observations regarding tissue reaction to implanted cyanoacrylate adhesives were noted in conjunction with the adhesive absorbability study:

TISSUE REACTION

| Adhesive | Acute Histotoxicity | | Encapsulation Thickness | | |
|---|---|---|---|---|---|
| | 6 Hr | 24 Hr | 1 Wk | 4 Wks | 2 Mos |
| a. MeC | 4 | 3 | Medium | Thick | Thin |
| b. IBC | 1 | 0 | Thin | Thin | Thin |
| c. CMeC | 3 | 1 | Medium | Medium – Thick | Thin |
| d. CEC | 3 | 1 | Medium | Medium – Thick | Thin |
| e. CIBC | 1 | 0 | Thin | Thin | Thin |
| f. COC | 1 | 0 | Thin | Medium – Thin | Thin |
| g. CHC | 1 | 0 | Thin | Thin | Thin |

In the above data, histotoxicity is rated visually from no inflammation (rated 0) to significant inflammation as generally associated with MeC (rated 4). It is thus apparent from these data that the cyanoacrylates of the instant invention, particularly the higher alkyl derivatives, have a low order of histotoxicity comparable to that commonly associated with non-absorbable IBC. It is similarly apparent from the encapsulation thickness data that the cyanoacrylates of the instant invention are also generally comparable to IBC in degree of tissue reactivity.

The preceding data illustrate that the cyanoacrylates of the present invention are generally well suited as absorbable tissue adhesives and demonstrate certain functional advantages over the isobutyl 2-cyanoacrylate of the prior art, particularly in regard to high absorbability associated with a low order of tissue reaction.

The preceding examples and evaluations are presented for purposes of illustrating certain preferred embodiments of the present invention. Many variations in these examples will be apparent to those skilled in the art, and the invention is accordingly not limited to the procedures, reactants, or results described in the examples.

What is claimed is:
1. A composition of the formula:

$$\boxed{D} \begin{array}{c} CH_2 \\ | \\ C \end{array} \begin{array}{c} CN \\ \diagdown \\ COOCH_2COOR \end{array}$$

wherein Ⓓ is a cyclic 1,3 diene and R is an organic radical having from 1 to about 12 carbon atoms.

2. A composition of claim 1 wherein Ⓓ is

[structure]

3. A composition of claim 2 wherein R is alkyl, alkenyl, or alkynyl or a halo- or alkoxy-substituted alkyl, alkenyl, or alkynyl group having from 1 to about 8 carbon atoms, cycloalkyl, aralkyl, aryl or substituted aryl.

4. A composition of claim 2 wherein R is alkyl having from 4 to 6 carbon atoms.

5. A composition of claim 2 wherein R is methyl, ethyl, allyl, n-butyl, isobutyl, hexyl, octyl, propargyl, 2-butoxyethyl, 2-ethoxyethyl, 2,2,2,-trifluoroethyl, cyclohexyl or benzyl.

6. A composition of the formula:

$$CH_2=C\begin{array}{c} CN \\ | \end{array}-C\begin{array}{c} O \\ \| \end{array}-O-C\begin{array}{c} R' \\ | \\ R' \end{array}-COOR$$

wherein R is an organic radical having from 1 to about 12 carbon atoms and each R' is individually hydrogen or methyl.

7. A composition of claim 6 wherein R is alkyl, alkenyl, or alkynyl or a halo or alkoxy-substituted alkyl, alkenyl, or alkynyl group having from 1 to about 8 carbon atoms, cycloalkyl, aralkyl, aryl or substituted aryl.

8. A composition of claim 6 wherein each R' is hydrogen.

9. A composition of claim 8 wherein R is alkyl having from 4 to 6 carbon atoms.

10. A composition of claim 8 wherein R is methyl, ethyl, allyl, n-butyl, isobutyl, hexyl, octyl, propargyl, 2-butoxyethyl, 2-ethoxyethyl, 2,2,2,-trifluoroethyl, cyclohexyl or benzyl.

11. A method of joining together two surfaces which comprises applying to at least one of said surfaces a compound of claim 6 and maintaining the surfaces in contact until said compound polymerizes.

12. A method of claim 11 wherein said surfaces comprise body tissue.

13. A method of claim 11 wherein one of said surfaces is body tissue and the other surface is a prosthetic device.

14. A method for repairing damaged living tissue to prevent the escape of fluids therethrough which comprises sealing said tissue with a film of a composition of claim 6.

15. A method for stemming the flow of blood from small vessels which comprises sealing said vessels with a hemostatic agent comprising a composition of claim 6.

16. A method of dressing burns to promote the healing thereof which comprises covering said burn with a precast film of a polymerized composition of claim 6.

17. A method of dressing wounds to promote the healing thereof which comprises covering said wound with a precast film of a polymerized composition of claim 6.

18. A method of dressing burns to promote the healing thereof which comprises coating the surface of said burn with a composition of claim 6.

19. A method of dressing wounds to promote the healing thereof which comprises coating the surface of said wound with a composition of claim 6.

* * * * *

UNITED STATES PATENT OFFICE
CERTIFICATE OF CORRECTION

Patent No. 3,995,541      Dated December 7, 1976

Inventor(s) Richard L. Kronenthal et al.

It is certified that error appears in the above-identified patent and that said Letters Patent are hereby corrected as shown below:

In Column 6, Title of Example 3, "10-ethanoanthracene-11-carboxylates (IV)" should read --- 10-ethanoanthracene-11-cyano-carboxylates (IV) ---.

In Column 8, Line 23, "H: 3,88" should read --- H: 3.88 ---.

In Column 9, Line 29, "Carbohexoymethyl" should read --- Carbohexoxymethyl ---.

In Column 9, Line 47, "crystalize" should read --- crystallize ---.

In Column 9, Line 55, "C: 62,90" should read --- C: 62.90 ---.

UNITED STATES PATENT OFFICE
CERTIFICATE OF CORRECTION

Patent No. 3,995,641  Dated December 7, 1976

Inventor(s) Richard L. Kronenthal et al.

It is certified that error appears in the above-identified patent and that said Letters Patent are hereby corrected as shown below:

In Column 11, Line 2, "160°-1702C" should read --- 160°-170°C ---.

In Claim 2, the formula 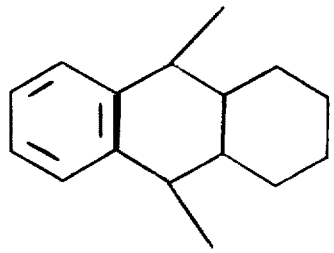 Should read 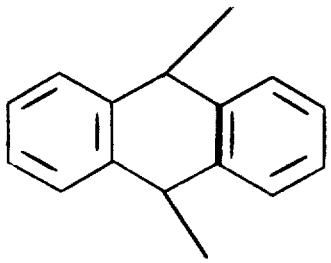

Signed and Sealed this

Thirteenth Day of September 1977

[SEAL]

Attest:

RUTH C. MASON
Attesting Officer

LUTRELLE F. PARKER
Acting Commissioner of Patents and Trademarks